United States Patent
Hsieh et al.

(10) Patent No.: US 9,560,432 B2
(45) Date of Patent: *Jan. 31, 2017

(54) BLUETOOTH COMMUNICATION BRACELET

(71) Applicant: 1MORE INC., Guangdong (CN)

(72) Inventors: Kuan-Hong Hsieh, Guangdong (CN);
Boqing Lin, Guangdong (CN);
Kun-Chih Hsieh, Guangdong (CN);
Kenneth Zhao, Guangdong (CN)

(73) Assignee: 1More Inc., Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/138,382

(22) Filed: Apr. 26, 2016

(65) Prior Publication Data

US 2016/0241942 A1 Aug. 18, 2016

Related U.S. Application Data

(63) Continuation of application No. 14/274,967, filed on May 12, 2014, now Pat. No. 9,332,338.

(30) Foreign Application Priority Data

Dec. 25, 2013 (CN) .......................... 2013 1 0726266
Jan. 24, 2014 (CN) .......................... 2014 1 0036758

(51) Int. Cl.
*H04R 1/10* (2006.01)
*H04R 1/02* (2006.01)
(Continued)

(52) U.S. Cl.
CPC .............. *H04R 1/028* (2013.01); *A61B 5/024* (2013.01); *A61B 5/746* (2013.01); *H04R 1/08* (2013.01);
(Continued)

(58) Field of Classification Search
None
See application file for complete search history.

(56) References Cited

U.S. PATENT DOCUMENTS

| 6,882,955 B1 * | 4/2005 | Ohlenbusch ......... A43B 3/0005 324/160 |
| 7,534,206 B1 * | 5/2009 | Lovitt ................ A61B 5/02438 482/8 |

(Continued)

FOREIGN PATENT DOCUMENTS

| CN | 200947172 Y | * 9/2007 |
| CN | 202587325 U | * 12/2012 |

(Continued)

*Primary Examiner* — Brenda Bernardi
(74) *Attorney, Agent, or Firm* — Rosenberg, Klein & Lee

(57) ABSTRACT

A Bluetooth communication bracelet includes a main body and a Bluetooth earphone. The main body includes a wearing member, a charging plate, an USB interface, and an audio jack. The wearing member defines a receiving groove, a positioning portion and a charging electrode. The receiving groove is located on the outer peripheral of the wearing member, the positioning portion. The charging electrode is located on sidewalls of the receiving groove. The charging plate is located in the wearing member. The USB interface is electrically coupled to the charging plate for charging the charging plate. The Bluetooth earphone, which is received in the receiving groove, includes a carrier, an earplug, and a microphone. The carrier sets a matching portion and a contact electrode. The matching portion matches the positioning portion to make the Bluetooth earphone releasably mounted to the wearing member. The contact electrode is in contact with the charging plate.

18 Claims, 4 Drawing Sheets

(51) Int. Cl.
*A61B 5/024* (2006.01)
*A61B 5/00* (2006.01)
*H04R 1/08* (2006.01)

(52) U.S. Cl.
CPC ............ *H04R 1/105* (2013.01); *H04R 1/1016* (2013.01); *H04R 1/1025* (2013.01); *H04R 1/1041* (2013.01); *H04R 1/1066* (2013.01); *H04R 2201/023* (2013.01); *H04R 2420/07* (2013.01); *H04R 2420/09* (2013.01)

(56) References Cited

U.S. PATENT DOCUMENTS

| | | | |
|---|---|---|---|
| 2007/0042821 A1* | 2/2007 | Lee | H04M 1/6066 455/575.6 |
| 2008/0152183 A1* | 6/2008 | Janik | H04M 1/05 381/375 |
| 2010/0217096 A1* | 8/2010 | Nanikashvili | A61B 5/02438 600/301 |
| 2012/0194976 A1* | 8/2012 | Golko | G06F 1/163 361/679.01 |
| 2014/0273858 A1* | 9/2014 | Panther | A61B 5/0002 455/41.2 |
| 2015/0172429 A1* | 6/2015 | Cai | H04M 1/0258 455/41.2 |

FOREIGN PATENT DOCUMENTS

| | | | | |
|---|---|---|---|---|
| CN | 202750212 U | * | 2/2013 | |
| CN | 202919208 U | * | 5/2013 | |
| CN | WO 2013149541 A1 | * | 10/2013 | ......... H01R 13/2421 |
| CN | 103429032 A | * | 12/2013 | |
| CN | 103441784 A | * | 12/2013 | |
| IT | WO 2013045983 A1 | * | 4/2013 | ............. H04B 1/385 |

\* cited by examiner

BLUETOOTH COMMUNICATION BRACELET

REFERENCE TO RELATED APPLICATION

This Application is being filed as a Continuation Application of patent application Ser. No. 14/274,967, filed 12 May 2014, currently pending.

FIELD OF THE INVENTION

The invention relates to a Bluetooth electrical device, especially a Bluetooth communication bracelet having Bluetooth earphone.

BACKGROUND OF THE INVENTION

With the rapid development of science and technology and the demands for life, the earphone has been widely applied in telephone communication, music transmission, and the like. Especially the appearance of wireless Bluetooth earphone helps people get rid of the dependence of headphone cable.

Bluetooth is a radio technology for short-range (usually within 10 m) devices communications, by which the information can be exchanged wirelessly between various devices, such as mobile phones, PDA, wireless earphones, laptops, peripherals and other related equipments.

Bluetooth earphone is a hands-free earphone based on the Bluetooth technology, which allows the users to get rid of annoying cables and to speak freely. The Bluetooth earphone has, since its appearance, become an outstanding tool to improve the efficiency of the mobile commerce.

However, in one aspect, the conventional Bluetooth earphone is an independent device, which is separated from other electronic devices such as mobile phones, thus it is inconvenient for carrying and cannot be properly placed if not in used. In addition, subject to volume restrictions, the battery of conventional Bluetooth earphone is limited and may not be charge in time, which results a poor endurance of conventional Bluetooth earphone.

DETAILED DESCRIPTION OF THE EMBODIMENTS

For easy understanding of the present invention, the following will describe more comprehensively about the invention according to the relevant diagrams. The diagrams provide the better embodiment of the invention. However, the invention may be implemented in many different forms and is not limited to the embodiments described herein. Inversely, these embodiments are provided to more thoroughly and comprehensively understand the present disclosure.

It should be noted that, when an element is referred to as "fixed to" another element, it can be directly on the other element or middle elements can be existed. When an element is considered as "connect to" another element, it can be directly connected to another element or middle elements can be simultaneously existed. In contrast, when an element is referred to as being "directly on", the middle element is not existed. As used herein, the terms "vertical", "horizontal", "left", "right" and other similar expressions is for the purposes of illustration only.

Unless otherwise defined, all of the technical and scientific terms used in the invention belonging to the technical field are the same as commonly understood meaning of the technical person in the field. In the description herein, the terms used in the present invention is only for the purpose of describing particular embodiments, and is not intended to limit the invention. As used herein, the term "and/or" includes one or more of the associated listed items and all combinations.

Figure 1:
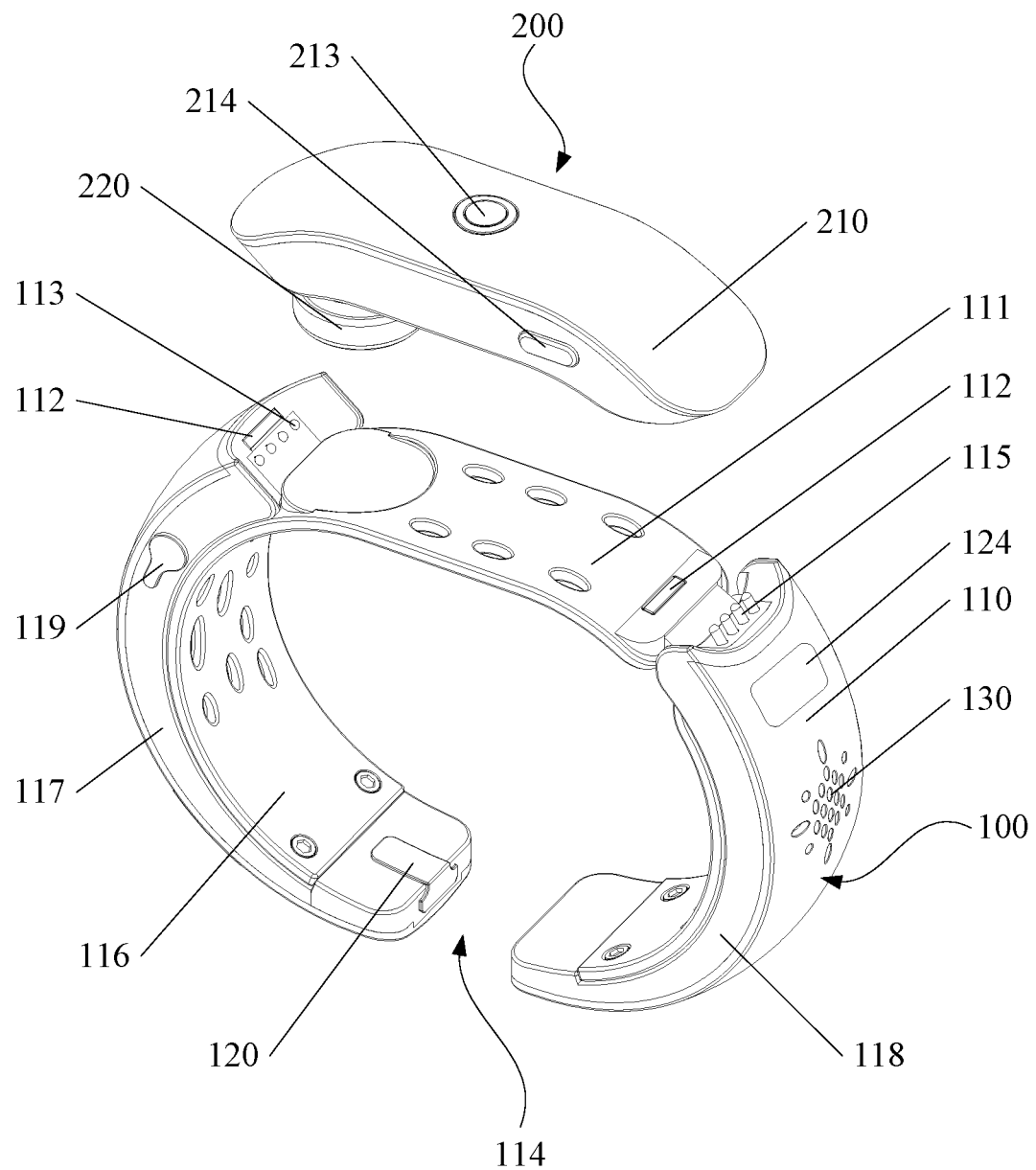
FIG. 1 is a structure diagram of Bluetooth communication bracelet according to one embodiment of the invention.
Figure 2:
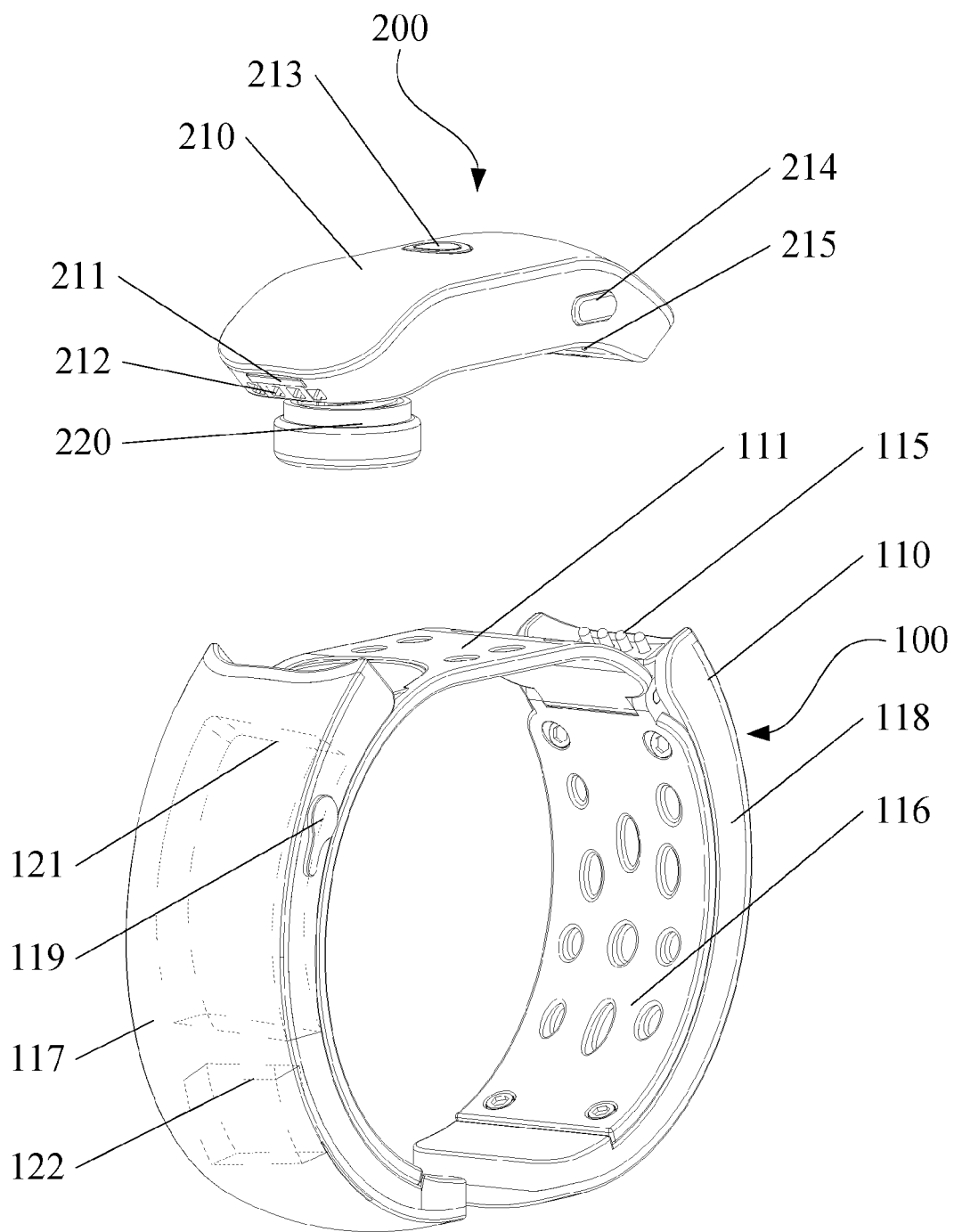
FIG. 2 is a structure diagram of another view of Bluetooth communication bracelet.

Referring to FIG. 1 and FIG. 2, a first embodiment of a Bluetooth communication bracelet includes a main body 100 and a Bluetooth earphone 200 removably mounted to the main body 100.

The main body 100 is shaped as a bracelet and includes a wearing member 110 and a charging plate 121. The wearing member 110 has an annular shape and defines a receiving groove 111 located on an outer peripheral of the wearing member 110. The wearing member 110 further includes a positioning portion 112 and a charging electrode 113 respectively located on opposite sidewalls of the receiving groove 111.

The charging plate 121 is located in the wearing member 110 and is electrically coupled to the charging electrode 113.

The wearing member 110 sets an USB interface 120 and an audio jack 119. The USB interface 120 is electrically coupled to the charging plate 121 for charging the charging plate 121. Additionally, the USB interface 120 and the audio jack 119 sets a casing, respectively. One end of the casing is fixed to the wearing member 110, and the other end of the casing is releasably connected to the wearing member 110. When using the USB interface 120 and the audio jack 119, the other end of the casing can be released; when not in use, the other end of the casing can be received in the wear member 110.

The Bluetooth earphone 200 can be received in the receiving groove 111, as shown in FIG. 2. The Bluetooth earphone 200 includes a carrier 210, an earplug 220, and a microphone 215.

The carrier 210 sets a matching portion 211 and a contact electrode 212. The matching portion 211, which is located at an end surface of the carrier 210, is cooperated with the positioning portion 112 to allow the Bluetooth earphone 200 to be removably mounted to the main body 100. The contact electrode 212, which is also located at the end surface of the carrier 210, can be in contact with the charging electrode 113 for charging the Bluetooth earphone 200. The contact electrode 212 can also be electrically coupled to the audio jack 119 to transmit audio signal between the Bluetooth earphone 200 and audio jack 119.

The earplug 220 is located on a side of the carrier 110 abutting against a bottom of the receiving groove 111.

The microphone 215 is located on the carrier 110, specifically, on the other end of the side of the carrier 110 abutting against a bottom of the receiving groove 111.

When the Bluetooth earphone 200 is removed from the receiving groove 111, it can answer an incoming call automatically; when the Bluetooth earphone 200 is placed in the receiving groove 111, the call will be hung up and the Bluetooth earphone 200 will started to be charged.

The earplug 220 is located on a side of the carrier 210 abutting against a bottom of the receiving groove 111. The earplug 220 is contractive and can be received in the carrier 210. When the Bluetooth earphone 200 is detached from the main body 100, the earplug 220 can be extended automatically outside the carrier 210.

Preferably, in order to enhance the convenience of wearing, the wearing member 110 defines a gap 114 on an edge of the wearing member 110. The receiving groove 111 and the gap 114 are symmetrically disposed relative to a center of wearing member 110. The size of the gap 114 can be changed by squeezing and deforming the wearing member 110, thus the size of the wearing member 110 can be adjusted.

In the illustrated embodiment, the wearing member 110 includes a metal ring 116, a first housing 117, and a second housing 118. The first housing 117 and the second housing 118 are located on an outer periphery of the metal ring 116 adjacent to the gap 114 of the wearing member 110. The first housing 117, the second housing 118, and a middle portion of the metal ring 116 cooperatively form the receiving groove 111.

The charging plate 121 is received in the wearing member 110 and is electrically coupled to the charging electrode 113. In the illustrated embodiment, the charging plate 121 is received in the first housing 117 of the wearing member 110.

The USB interface 120 is located on an end of the first housing 117 of the wearing member 110 adjacent the gap 114.

Furthermore, the main body 100 includes a speaker 130 located at an outer peripheral of the wearing member 110. In the illustrated embodiment, the speaker 130 is located at the second housing 118. When the Bluetooth earphone 200 is received in the receiving groove 111, the speaker 130 is electrically coupled to the Bluetooth earphone 200 via a connecting electrode 115; and when the Bluetooth earphone 200 is removed from the receiving groove 111, the speaker 130 is power off.

Furthermore, the wearing member 110 sets a music player 122 therein, which is electrically coupled to the charging plate 121 and the audio jack 119, respectively.

Furthermore, the wearing member 110 sets a human parameter detector for measuring human body parameters and an indicator to alert the user based upon the analysis of the human body parameters.

Preferably, the human parameter detector is a reflection-type sensor located on the wearing member 110. The reflection-type sensor includes a green light LED. The green light emitted by the LED is irradiated to human parts such as the finger, and the pulse can be detected by measuring the reflection light. In alternative embodiment, the human body parameter detector may be sensing contacts located on the wearing member 110. In this case, the pulse can be detected via the contact of the sensing contact with the wrist.

The indicator is an LED located on the carrier 210 of the Bluetooth earphone 200. After analyzing the pulse detected by the human parameter detector, the LED flashes different colors or different frequency based upon the analysis results, so as to indicate the user's emotional state and remind the user to regulate emotions. In alternative embodiment, the indicator may be a vibrator located on the carrier 210 of the Bluetooth earphone 200. The vibrator can vibrate based upon the analysis results, so as to remind the user to regulate emotions.

The main body 100 further includes a monitor located on the wearing member 110 for displaying local time and call time. In the illustrated embodiment shown in FIG. 1, the monitor is a display screen 123 located at the second housing 118 of the wearing member 110. In alternative embodiment, the monitor can be a plurality of LEDs located at the wearing member 110 arranging in a clock-like circle or square. In alternative embodiment, the monitor may be an E-ink display.

In other embodiment, the monitor is replaced by the LED of the indicator to display local time and call time.

The carrier 210 sets an answer key 213 and the power key 214. The answer key 213 is used to control the answer or hang-up of the Bluetooth earphone 200. The LED used as the indicator can be integrated in the answer key 213. Preferably, the answer key 213 is located on a side of the carrier 210 away from the earplug 220. The power key 214 is used to control the power of the Bluetooth earphone 200.

In the illustrated embodiment, one of the positioning portion 112 and the matching portion 211 is a first magnet, the other one is a second magnet or iron piece attracted to the first magnet. By the magnetic attraction between the positioning portion 112 and the matching portion 211, the Bluetooth earphone 200 can be positioned in the receiving groove 111 of the wearing member 110 of the main body 100.

Furthermore, the number of the positioning portion 112 is two, and the two positioning portions 112 are located at opposite sidewalls of the receiving groove 111 of the wearing member 110. The number of the matching portion 211 is two, and the two matching portions 211 are located at both end surfaces of the carrier 210. The two positioning portions 112 mate with the two corresponding matching portions 211, such that both ends of the carrier 210 of the Bluetooth earphone 200 are positioned, therefore the Bluetooth earphone 200 is firmly received in the receiving groove 111.

Furthermore, the two opposite sidewalls of the receiving groove 111 of the wearing member 110 define two curved recesses, and the both ends of the carrier 210 of the Bluetooth earphone 200 are curved to match with the two curved recesses of the two opposite sidewalls of the receiving groove 111 of the wearing member 110, such that the Bluetooth earphone 200 is further positioned to avoid shaking of the Bluetooth earphone 200 in the receiving groove 111 of the wearing member 110.

Furthermore, the carrier 210 sets a handle portion (not labeled) located at each side of the carrier 210 to increase a surface friction, thus facilitating the remove of the Bluetooth earphone 200. For example, the handle portion can be ribs or rubber layers located at each side of the carrier 210.

In the illustrated embodiment, the carrier 210 defines a receiving hole on a side of the carrier 210 abutting the bottom of the receiving groove 111 and sets an elastic member located in the receiving hole. The earplug 220 can be received in the receiving hole and can be bounced outside of the receiving hole by the resilient force of the elastic member.

Figure 4:
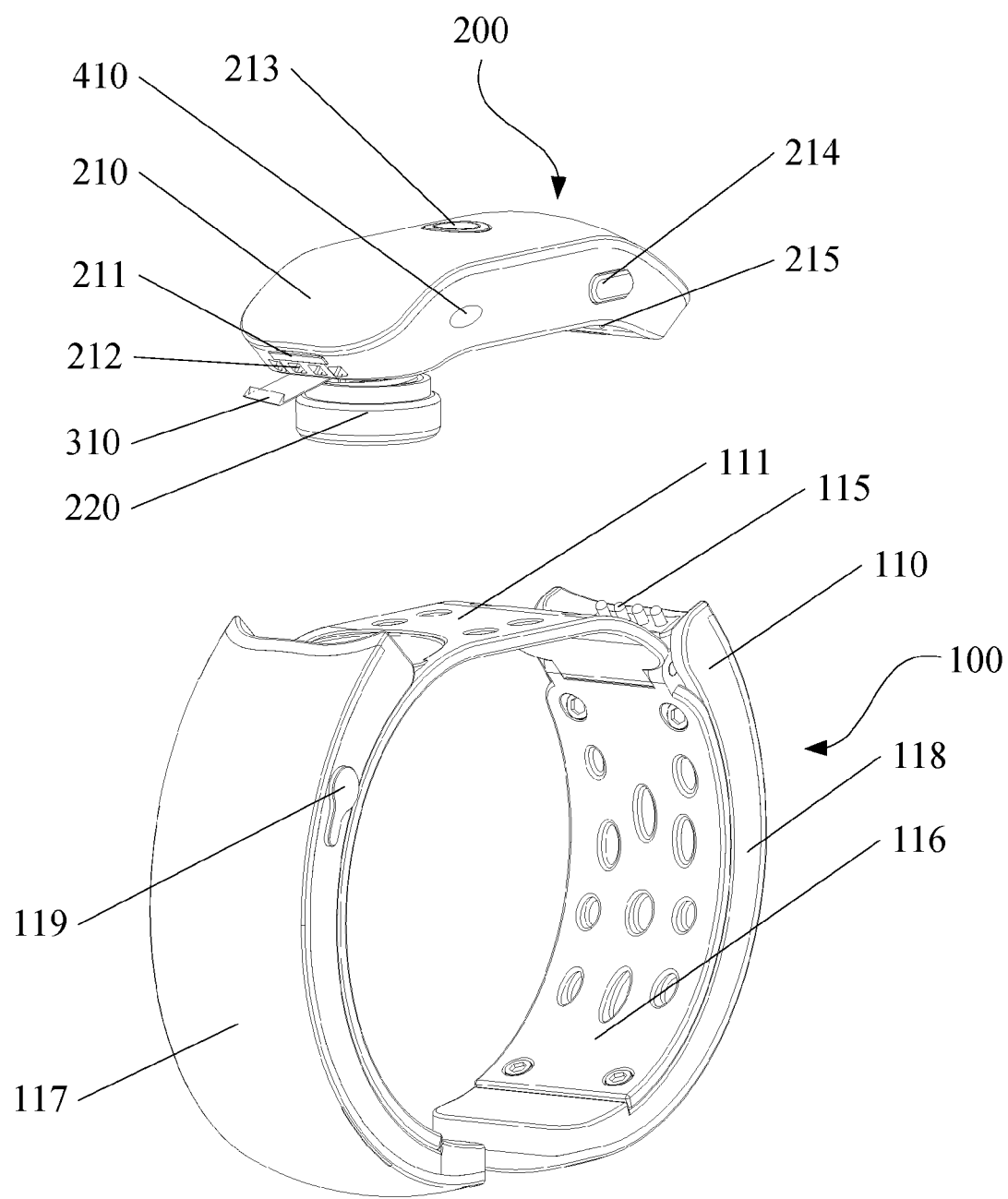
FIG. 4 is a using structure diagram of Bluetooth communication bracelet according to other embodiment of the invention.

Referring to FIG. 4, a second embodiment of a Bluetooth bracelet 20 is similar to the first embodiment of the Bluetooth bracelet, the difference lies in that: the positioning portion of the wearing member 110 of the Bluetooth bracelet is a latching slot (not shown) located on a side wall of the receiving groove 111, and the matching portion 211 of the carrier 210 of the Bluetooth bracelet is a latching hook 310 located on the carrier 210. The carrier 210 further sets a latching button 410 to control the stretch or retraction of the latching hook 310.

It should be noted that, the positioning portion of the wearing member of the main body and the matching portion of the carrier of the Bluetooth earphone are not limited to the structure described above. For example, in alternative embodiments, the number of the positioning portion can be two, i.e. the first and the second positioning portions, while the number of the matching portion is two, i.e. the first and the second matching portions corresponding to the first and the second positioning portions, respectively. One of the first positioning portion and the first matching portion is a first magnet, the other one is a second magnet or iron piece attracted to the first magnet. The second positioning portion is a latching slot located on a side wall of the receiving groove, and the second matching portion is a latching hook located on the carrier. The carrier further sets a latch button to control the stretch or retraction of the latching hook.

Figure 3:
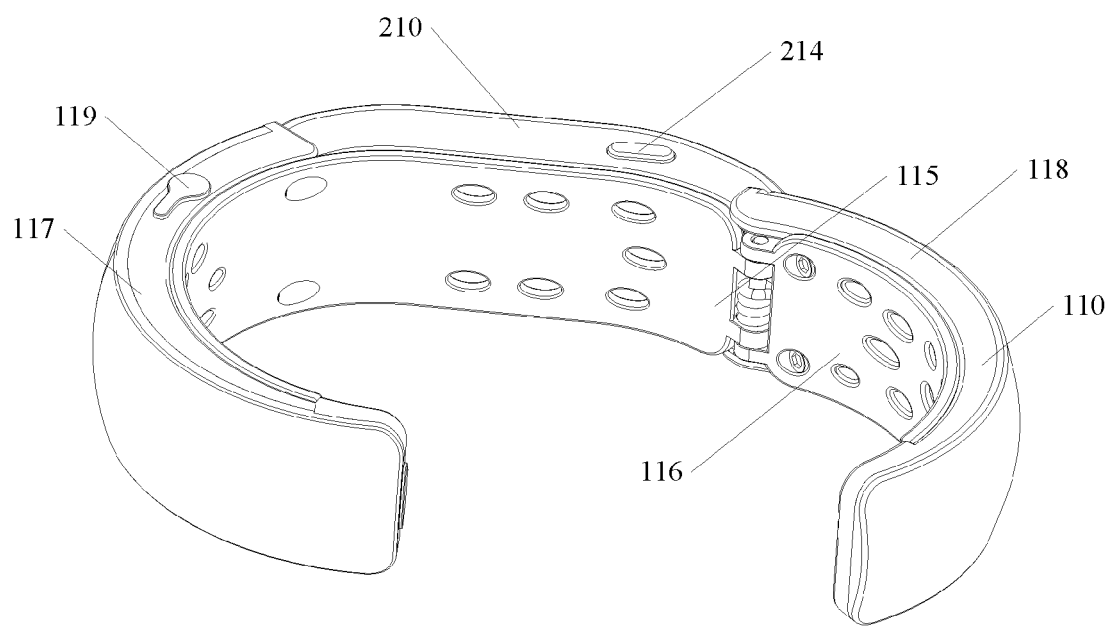
FIG. 3 is a using structure diagram of Bluetooth communication bracelet according to one embodiment of the invention.

Furthermore, the metal ring is formed by at least two pieces rotatably connected together. Preferably, as shown in FIG. 3, the piece of the metal ring 116 corresponding to the first housing 117 is rotatably connected to the piece of the metal ring 116 corresponding to the receiving groove 111, and/or the piece of the metal ring 116 corresponding to the second housing 118 is rotatably connected to the piece of the metal ring 116 corresponding to the receiving groove 111.

Compared with the conventional Bluetooth communication bracelet, the Bluetooth bracelet according to the present disclosure has at least the following advantages:

(1) When not in use, the Bluetooth earphone of the Bluetooth bracelet can be received in the receiving groove of the wearing member of the main body, and the earplug of the Bluetooth earphone is received in the carrier of the Bluetooth. The wearing member of the main body can be worn on the wrist or other parts of the body, and by mating the matching portion of the Bluetooth earphone and the positioning portion of the wearing member, the Bluetooth earphone is releasably mounted in the receiving groove of the wearing member to facilitating the portability. When answering the call using the Bluetooth earphone, it simply needs to remove the Bluetooth earphone from the receiving groove, and the earplug will be bounced outside of the carrier automatically. Therefore, the Bluetooth bracelet is easy to carry and convenient to answer phone calls.

(2) When not in use, the Bluetooth earphone of the Bluetooth bracelet can be received in the receiving groove of the wearing member of the main body, the wearing member sets the charging plate to charging the Bluetooth earphone. The charging plate is electrically coupled to the Bluetooth earphone via the charging electrode on the wearing member of the main body and the contact electrode on the Bluetooth earphone, such that the Bluetooth earphone can be charged freely. Therefore, the Bluetooth earphone of the Bluetooth bracelet has a longer endurance.

(3) The USB interface on the wearing member of the Bluetooth bracelet can be electrically coupled to an external power supply, thus charging the charging plate.

(4) The audio jack of the wearing member of the Bluetooth bracelet can be inserted by an external headphone to answer the Bluetooth earphone or output the audio signal of the music player.

(5) The metal ring of the wearing member of the Bluetooth bracelet is formed by at least two pieces rotatably connected together, thus facilitating the use.

The above embodiment describes only a number of implementations, the descriptions is concrete and detailed. Nevertheless, it will be understood that such embodiments are merely illustrative of and not restrictive on the broad invention. Under the premise without departing from the invention concept, it should be noted that the common technical person of this field can make some transformation and improvement which belongs to the protection scope of the invention. Hence, the protection scope of this invention should be subject to the illustrated claims.

What is claimed is:

1. A Bluetooth communication bracelet, comprising:
a main body including:
a wearing member contoured with an internal cavity extending inside of said wearing member along the length thereof, wherein the wearing member defines a receiving groove located on an outer peripheral of the wearing member, the wearing member further including a positioning portion and a charging electrode, each located on a respective sidewall of the receiving groove;
a charging plate located in said internal cavity formed in the wearing member, said charging plate being electrically coupled to the charging electrode;
a USB interface located on the wearing member, wherein the USB interface is electrically coupled to the charging plate for charging the charging plate;
a Bluetooth earphone received in the receiving groove, wherein the Bluetooth earphone includes:
a carrier, wherein the carrier has a matching portion and a contact electrode, wherein the matching portion cooperates with the positioning portion of said wearing member to allow the Bluetooth earphone to be removably mounted to the main body, wherein the contact electrode is positioned in contact with the charging electrode positioned at said wearing member for charging the Bluetooth earphone;
an earplug located on a side of the carrier abutting against the receiving groove;
a microphone located on the carrier, and
a music player located in said internal cavity formed in said wearing member and electrically coupled in said internal cavity to said charging plate.

2. The Bluetooth communication bracelet of claim 1, wherein the earplug is received in the carrier, and wherein when the Bluetooth earphone is removed from the main body, the earplug is extended automatically outside the carrier.

3. The Bluetooth communication bracelet of claim 1, wherein the carrier includes an answer key and a power key, the answer key being adapted to control answering or hanging up operations of the Bluetooth earphone, and wherein the power key is used to control power supply of the Bluetooth earphone.

4. The Bluetooth communication bracelet of claim 3, wherein one of the positioning portion of the wearing member and the matching portion of the carrier includes a first magnet, and wherein the other one of said positioning portion and the matching portion includes a second magnet or iron piece for cooperation with the first magnet.

5. The Bluetooth communication bracelet of claim 1, wherein the positioning portion includes a latching slot located on a side of the receiving groove, wherein the matching portion includes a latching hook located on the carrier, and wherein the carrier further includes a latching button to control stretching or retraction of the latching hook.

6. The Bluetooth communication bracelet of claim 3, wherein the positioning portion includes a first positioning portion and a second positioning portion, wherein the matching portion includes a first matching portion and a second matching portion corresponding to the first and the second positioning portion, respectively,
   wherein a respective one of the first positioning portion and the first matching portion includes a first magnet, and wherein the other one of said first positioning portion and first matching portion includes a second magnet or iron piece cooperating with the first magnet, and
   wherein the second positioning portion includes a latching slot located on a side wall of the receiving groove, and wherein the second matching portion includes a latching hook located on the carrier, the carrier further including a latch button to control stretching or retraction of the latching hook.

7. The Bluetooth communication bracelet of claim 3, wherein the wearing member further includes a human parameter detector for measuring human body parameters and an indicator to alert the user based upon the analysis of the human body parameters.

8. The Bluetooth communication bracelet of claim 2, wherein the carrier defines a receiving hole on a side of the carrier which abuts the bottom of the receiving groove and includes an elastic member located in the receiving hole, wherein the earplug is received in the receiving hole, and wherein the earplug is bounced outside of the receiving hole by the resilient force of the elastic member.

9. The Bluetooth communication bracelet of claim 1, wherein the wearing member defines a gap on an edge of the wearing member, wherein the receiving groove and the gap are symmetrically disposed about a center of wearing member, and wherein the size of the gap is changed by squeezing and deforming the wearing member.

10. The Bluetooth communication bracelet of claim 9, wherein the wearing member includes a metal ring, a first housing, and a second housing, wherein the first housing and the second housing are located on an outer periphery of the metal ring adjacent to the gap of the wearing member, wherein the first housing, the second housing and a middle portion of the metal ring cooperatively form the receiving groove, and
   wherein said first housing is formed with said internal cavity extending along substantially the entire length thereof, the charging plate being received in the first housing.

11. The Bluetooth communication bracelet of claim 10, wherein the metal ring is formed by at least two pieces rotatably connected together.

12. The Bluetooth communication bracelet of claim 10, wherein the main body includes a speaker located on the second housing.

13. The Bluetooth communication bracelet of claim 1, wherein the main body includes a monitor located on the wearing member.

14. A Bluetooth communication bracelet, comprising:
   a main body including:
      a wearing member contoured with an internal cavity extending inside of said wearing member along the length thereof, wherein the wearing member defines a receiving groove located on an outer peripheral of the wearing member, the wearing member further including a positioning portion and a charging electrode located on the same sidewall of the receiving groove;
      a charging plate located in said internal cavity formed in the wearing member, said charging plate being electrically coupled to the charging electrode;
      a USB interface located on the wearing member, wherein the USB interface is electrically coupled to the charging plate for charging the charging plate;
      a Bluetooth earphone received in the receiving groove, wherein the Bluetooth earphone includes:
      a carrier, wherein the carrier has a matching portion and a contact electrode, wherein the matching portion cooperates with the positioning portion of said wearing member to allow the Bluetooth earphone to be removably mounted to the main body, wherein the contact electrode is positioned in contact with the charging electrode positioned at said wearing member for charging the Bluetooth earphone;
      an earplug located on a side of the carrier abutting against the receiving groove;
      a microphone located on the carrier, and
      a music player located in said internal cavity formed in said wearing member and electrically coupled in said internal cavity to said charging plate.

15. The Bluetooth communication bracelet of claim 14, wherein the main body further comprises an audio jack located on the wearing member, wherein the contact electrode is electrically coupled to the audio jack, and the music player is electrically coupled to the audio jack located at said wearing member in contact with said internal cavity formed therein.

16. The Bluetooth communication bracelet of claim 14, wherein the carrier includes an answer key and a power key, the answer key being adapted to control answering or hanging up operations of the Bluetooth earphone, and wherein the power key is used to control power supply of the Bluetooth earphone.

17. The Bluetooth communication bracelet of claim 16, wherein the wearing member further includes a human parameter detector for measuring human body parameters and an indicator to alert the user based upon the analysis of the human body parameters.

18. The Bluetooth communication bracelet of claim 14, wherein the positioning portion includes a latching slot located on a side of the receiving groove, wherein the matching portion includes a latching hook located on the carrier, and wherein the carrier further includes a latching button to control stretching or retraction of the latching hook.

\* \* \* \* \*